US00PP10458P

United States Patent [19]

Fackler

[11] Patent Number: Plant 10,458

[45] Date of Patent: Jun. 23, 1998

[54] APPLE TREE NAMED 'BIG RED GALA'

[75] Inventor: Edward Fackler, New Salisbury, Ind.

[73] Assignee: Protree Nurseries, Brentwood, Calif.

[21] Appl. No.: 770,490

[22] Filed: Dec. 20, 1996

[51] Int. Cl.[6] ..... A01H 5/00

[52] U.S. Cl. ..... Plt./34.1

[58] Field of Search ..... Plt./34.1

*Primary Examiner*—James R. Feyrer

*Attorney, Agent, or Firm*—Klarquist Sparkman Campbell Leigh & Whinston, LLP

[57] ABSTRACT

A new and distinct variety of Gala apple tree named 'Big Red Gala' characterized by large fruit size, attractive medium red blush, larger leaves, and rounder fruit than standard Gala.

3 Drawing Sheets

BACKGROUND OF THE INVENTION

The present invention comprises a new and distinct variety of Gala apple tree (*Malus domestica*), referred to by the varietal name 'Big Red Gala'.

The originally discovered sport of the present tree of the new variety was a limb sport or mutation of Gala variety Gala/M7 (U.S. Plant Pat. No. 3,637). This new tree was discovered by me in a cultivated area in New Salisbury, Ind. I was first attracted to this new variety by the large fruit size.

The new tree 'Big Red Gala' has been asexually reproduced by both grafting and budding at Rocky Meadow Orchard & Nursery, New Salisbury, Ind.

The 'Big Red Gala' variety was compared to the Gala/M7 variety. The comparisons in this description are of trees growing on the same rootstock (M7). Fruit shown in the figures were grown at Rocky Meadow Orchard, New Salisbury, Ind., and were from trees of similar age.

This invention has not been observed under all possible environmental conditions. The phenotype may vary significantly with variations in environment such as temperature, light intensity, and daylength, without any variation in genotype. However, the following combination of traits have been repeatedly observed in asexually propagated progeny and are determined to be the basic characteristics of this invention, which in combination distinguish 'Big Red Gala' as a new and distinct variety: (1) significantly larger fruit size; (2) attractive medium red blush; (3) larger leaves; and (4) rounder shape of fruit than standard Gala (which is round-conical). Asexual propagation shows that this unique combination of characteristics hold true to form and are established and transmitted through succeeding propagations.

BRIEF DESCRIPTION OF THE PHOTOGRAPHS

The accompanying photographs show typical specimens of 'Big Red Gala' and distinctive features thereof in color as nearly true as is reasonably possible to make the same in a color illustration of this character.

DETAILED DESCRIPTION

Figure 1:
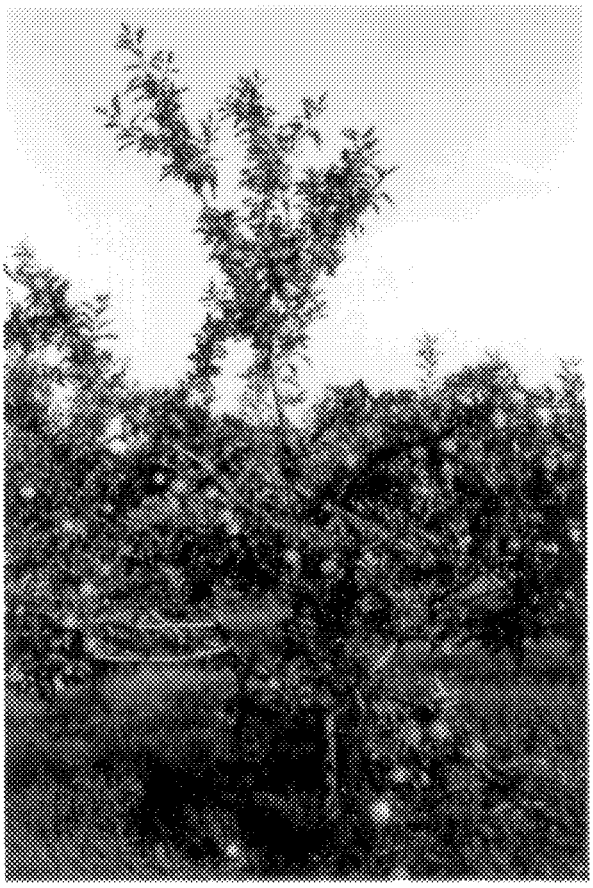
FIG. 1 is a view of the parent Gala/M7 tree showing the limb mutation with extremely large-sized fruit that was asexually propagated to produce the tree of the present invention.
Figure 2:
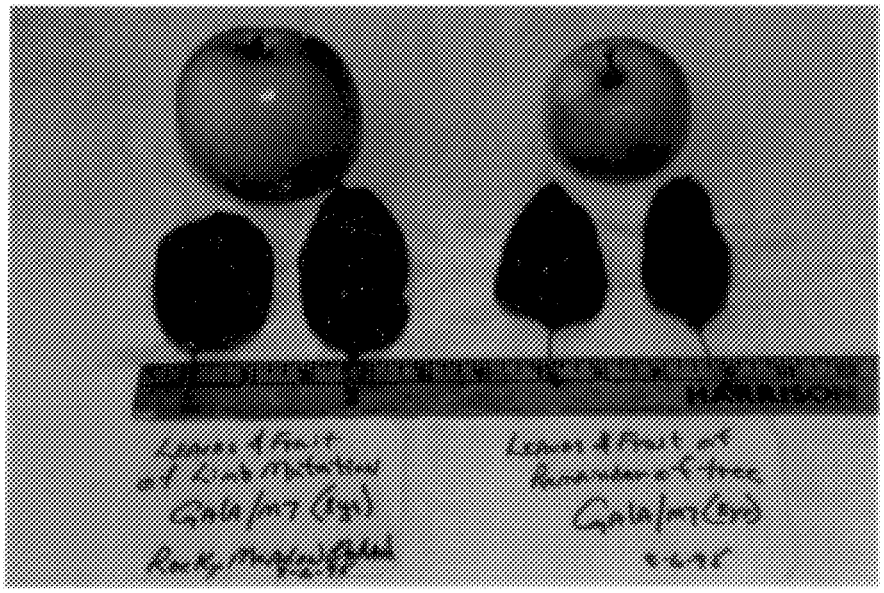
FIG. 2 shows fruit and leaves of 'Big Red Gala' and of Gala/M7.
Figure 3:
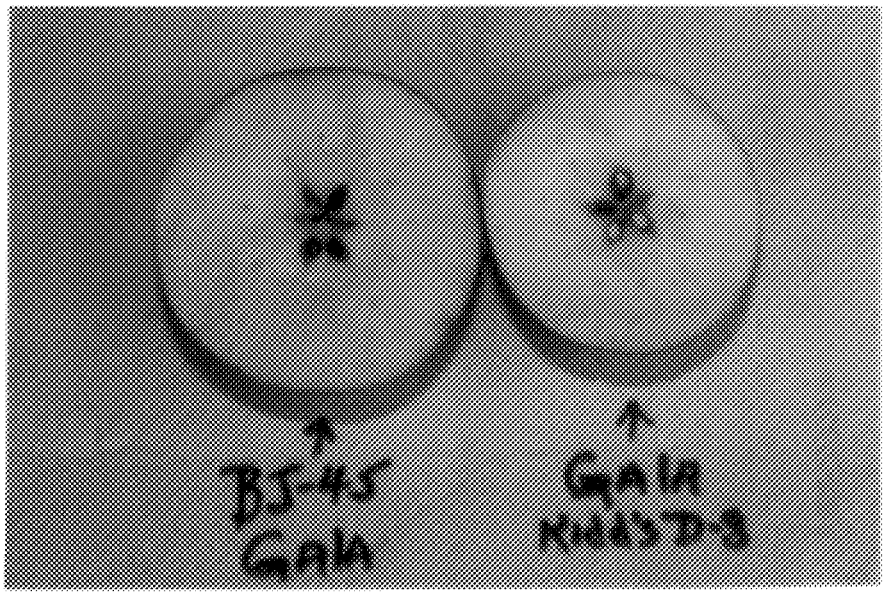
FIG. 3 is a cross-sectional view of fruit of harvest maturity of 'Big Red Gala' (left, labeled 'BJ-45 Gala') and of 'Gala Kidd's D-8' (right).

The following is a detailed description of the invention based on plants produced under orchard conditions in New Salisbury, Ind., and observed at this location in August 1996. All trees were of productive maturity.

Color references are made in accordance with The Royal Horticultural Society color standards, except where the use of general color terms of ordinary dictionary significance is obvious.

All trees of the new variety, insofar as I have been able to observe them, have been identical in all the characteristics described below.

Species: *Malus domestics.*

Parentage: Limb sport of Gala/M7.

Propagation: Holds to distinguishing characteristics through succeeding propagation by grafting and budding.

Locality where grown and observed: Rocky Meadow Orchard, New Salisbury, Ind.

Dates of first and last picking: August 19 to August 23.

Tree

- *Size.*—Medium-small.
- *Vigor.*—Initially vigorous, but slowing quickly.
- *Habit.*—Semi-spur (similar to Gala).
- *Trunk.*—Smooth.
- *Branches.*—Medium strong or thick.
- *Lenticels.*—Many — 80 per inch, small (0.05 mm×1 mm), light grey to tan (RHS 1598) .
- *Leaves.*—Size: Length, 12 cm. Width, about 6.5 cm. Shape: Oval-pointed. Color: Medium dark green (RHS 143A). Margin: Serrate. Petiole: Thick — 28 mm long.
- *Flower.*—Size: Medium, larger than Gala. Color: White when open, pink before opening. Flowering period: April 22–April 29. Pollinators: Any diploid in same season.

Fruit: Maturity when described was eating ripe.

- *Size.*—Large to very large — 350 to 380 grams.
- *Shape.*—Rounder than standard Gala varieties (9 cm wide, 6 cm tall).
- *Cavity.*—Narrow and deep, acute.
- *Basin.*—Wide with slight scarf skin.
- *Stem*—Medium thick, 24 mm long.
- *Calyx.*—Closed, small.
- *Locules* (*carpels*).—6.

Skin:

- *Ground color.*—Whitish yellow (RHS 154D).
- *Color markings.*—Flushed with red flecks.

*Color of markings.*—Undercolor faded red, blush medium red (RHS 42A).

*Lenticels.*—Many, small.

*Color of lenticels.*—Creamy white.

*Overcolor.*—Medium red (RHS 42A).

*General color effect.*—Attractive medium red with excellent finish.

*Flesh.*—Creamy white. Texture: Crisp, juicier than Gala. Flavor: Rich and aromatic, similar to Gala.

*Quality.*—Excellent.

*Core.*—Bundle area: Rectangular, 19 mm×16 mm. Bundles: 6. Core lines: Medium thick, ovate. Calyx-tube: Closed-small or short. Seed cells: 6. Cell walls: Thin.

*Seeds.*—9–12. Number in one cell: 1 or 2. Length: 9 mm. Breadth: 6 mm. Color: Dark brown.

*Use.*—Fresh eating — dessert.

*Keeping quality.*—Good, 3 months in common refrigerator.

*Production.*—Very good.

Resistance to insects and disease: None noted.

The trees of the 'Big Red Gala', insofar as they have been observed, are essentially the same in growth characteristics (vigor, limb angle, spur development) as 'Gala' (Kidd's D-8). The ploidy of the 'Big Red Gala' variety has been examined and this variety appears to be diploid.

The leaf size of leaves from trees of the 'Big Red Gala' variety has been observed to be ten to fifteen percent larger than the leaf size of comparable leaves from trees of the 'Kidd's D-8 Gala' variety. In addition, flowers from trees of the 'Big Red Gala' variety have been observed to be larger than those of trees of the 'Kidd's D-8 Gala' variety by ten to fifteen percent.

The fruit of the 'Big Red Gala' variety is a blush red with no identifiable striping. The intensity of the color of the fruit of the new variety is somewhat greater than the intensity of fruit of the 'Kidd's D-8 Gala' variety. Harvest dates have been observed to be the same for both the 'Big Red Gala' and 'Kidd's D-8 Gala' varieties.

Fruit of the 'Big Red Gala' variety have shown no physical disorder, such as water core, even after three months of storage. However, storage duration may be about five percent less for 'Big Red Gala' variety fruit than 'Kidd's D-8 Gala' variety fruit due perhaps to the larger fruit cell size of apples from 'Big Red Gala' trees.

The productivity of 'Big Red Gala' variety trees is very good and appears to be equal to the productivity of 'Kidd's D-8 Gala' trees.

I claim:

1. A new and distinct variety of Gala apple tree substantially as herein shown and described.

* * * * *